United States Patent [19]
Kitakaze et al.

[11] Patent Number: 5,571,524
[45] Date of Patent: Nov. 5, 1996

[54] AGENT FOR CURING ISCHEMIC MYOCARDIAL DISEASE

[75] Inventors: Masafumi Kitakaze, Izumi; Masatsugu Hori, Kobe; Takenobu Kamada, Kyoto; Hiroshi Nakajima, Uji; Akihiro Sekine; Tetsuaki Yamaura, both of Tokyo, all of Japan

[73] Assignees: Unitika Ltd., Amagasaki; Fujirebio, Inc., Tokyo, both of Japan

[21] Appl. No.: 473,774

[22] Filed: Jun. 6, 1995

[30] Foreign Application Priority Data

Jun. 30, 1994 [JP] Japan .................. 6-149971

[51] Int. Cl.$^6$ .................. A61F 2/02; A61K 9/48; A61K 31/715
[52] U.S. Cl. .................. 424/423; 424/434; 424/435; 424/451; 424/464; 424/489; 514/46; 514/47; 514/48
[58] Field of Search .................. 424/423, 434, 424/435, 451, 464, 489; 514/46, 47, 48; 536/26, 27

[56] References Cited

U.S. PATENT DOCUMENTS

| | | | |
|---|---|---|---|
| 5,049,550 | 9/1991 | Zamecnik | 514/47 |
| 5,219,841 | 6/1993 | Inaba et al. | 514/47 |
| 5,306,629 | 4/1994 | Yamamioto et al. | 435/87 |
| 5,380,715 | 1/1995 | Sekine et al. | 514/47 |

*Primary Examiner*—Carlos Azpuru
*Attorney, Agent, or Firm*—Oblon, Spivak, McClelland, Maier & Neustadt, P.C.

[57] ABSTRACT

An agent for curing ischemic myocardial disease which contains an effective amount of diadenosine 5',5'''-p$^1$,p$^4$-tetraphosphate (Ap4A) of formula (I):

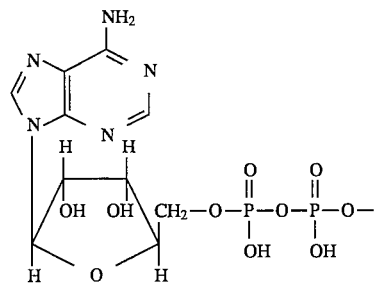
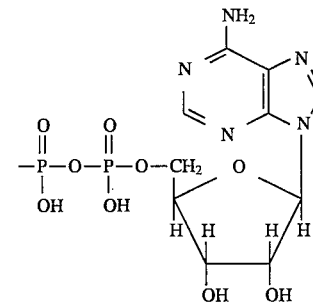

or a pharmaceutically-acceptable salt thereof.

4 Claims, No Drawings

AGENT FOR CURING ISCHEMIC MYOCARDIAL DISEASE

BACKGROUND OF THE INVENTION

1. Field of the Invention

The present invention relates to an agent for curing ischemic myocardial disease comprising an effective amount of diadenosine 5',5'''-$p^1$,$p^4$-tetraphosphate or a pharmaceutically-acceptable salt thereof.

2. Discussion of Background

Angina pectoris and myocardial infarction are diseases that cause heart failure, which occur when coronary blood flow is stopped or considerably reduced as a result of coronary vessel atherosclerosis and thrombosis, triggering an imbalance in oxygen supply to the cardiac muscle. Such diseases are collectively referred to as ischemic myocardial disease.

It is said that at the tame of ischemic myocardial attack, it is extremely important to expand the coronary vessel to sufficiently improve blood flow as quickly as possible.

This is crucial because the longer the ischemic attack, the greaterthe the risk that the impairment to the myocardial function and coronary vessel will become irreversible. To prevent this, vasodilators such as nitroglycerin or thrombolytic agents are used. However, these agents are not always effective and many times their effect is either insufficient or totally irrelevant. In that case, for instance, percutaneous transluminal coronary angioplasty (PTCA) and a coronary bypass operation (grafting of peripheral arteries or venae) are carried out.

Ischemic preconditioning (IP) was first discovered by Murry, C. E., Jennings, R. B. and Reimer, K. A. as reported in "Preconditioning with ischemia: a delay of lethal cell injury in ischemic myocardium" in Circulation 74, 1124–1136, 1986. Later, ischemic preconditioning using adenosine was conducted by Liu, G. S., Van Winkkle, D. M. et al. as reported in "Protection against infarction afforded by preconditioning is mediated by $A_1$ adenosine receptors in rabbit heart" in Circulation 84, 350–356, 1991.

The experimental discovery of ischemic preconditioning (IP) revealed that by causing a short (2–5 min.) myocardial ischemia to occur once or several tames prior to a long myocardial ischemia, resistance against the longer attack increases. When IP is conducted, the amount Of endogenous adenosine increases. In view of this, adenosine is considered as an endogenous compound capable of protecting cardiac muscle against ischemia.

In the course of the search for a better cardiac muscle protection against ischemia to replace adenosine, the inventors of the present invention discovered that diadenosine 5',5'''-$p^1$,$p^4$-tetraphosphate was capable of increasing coronary blood flow—even in ischemic states in which adenosine failed—and of exhibiting a myocardial protection effect against ischemia.

These phenomena obviously indicate that diadenosine 5',5'''-$p^1$,$p^4$-tetraphosphate has a myocardial protection mechanism different from that of adenosine.

Diadenosine 5',5'''-$p^1$,$p^4$-tetraphosphate is known to have such bioactivities as an ADP-induced human platelet aggregation inhibitory effect (J. Leuthje and A. Ogiluie, Biochem. Biophys. Res. Commun., 118, 704, 1984), a vasodilating effect on rabbit mesenteric arteries (R. Busse et al. Am. J. Physiol., 254, 828, 1988), an anti-arrhythmia effect (Japanese Laid-Open Patent Application 3-167126), a deliberated hypotensive effect (Japanese Laid-Open Patent Application 5-286861), and a vasodilating effect on coronary vessels at normal time.

However, as for no reports have ever confirmed the possibility that diadenosine 5',5'''-$p^1$,$p^4$-tetraphosphate can be used as an agent for curing ischemic myocardial disease based on the discovery that diadenosine 5',5''' -$p^1$,$p^4$-tetraphosphate is capable of increasing coronary blood flow even in a state of excessive myocardial ischemia and also capable of exhibiting a myocardial protection effect against ischemia.

SUMMARY OF THE INVENTION

It is therefore an object of the present invention to provide an agent for curing ischemic myocardial disease capable of increasing coronary blood flow even in a state of excessive myocardial ischemia and of exhibiting a myocardial protection effect against ischemia.

The object of the present invention can be achieved by an agent for curing ischemic myocardial disease, which comprises diadenosine 5',5'''-$p^1$, $p^4$-tetraphosphate or a pharmaceutically-acceptable salt thereof in an effective amount, which may be admixed with a pharmaceutically-acceptable carrier or diluent.

DESCRIPTION OF THE PREFERRED EMBODIMENTS

Diadenosine 5',5'''-$p^1$, $p^4$-tetraphosphate (hereinafter referred to as Ap4A) is a novel type of nucleotide present in the body having the following structural formula:

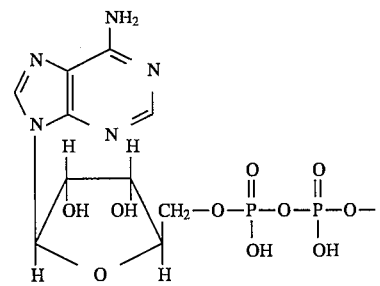

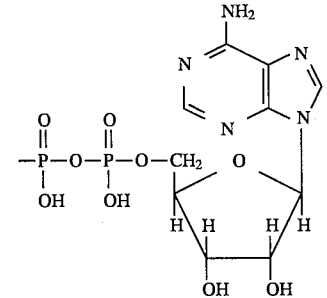

Ap4A can be produced by conventional organic synthesis using ATP as a starting material, or by enzyme synthesis using, for instance, bacillus-stearothermophilus-induced aminoacyl tRNA synthetase (Japanese Laid-Open Patent Application 62-278992, and Agricultural and Biological Chemistry, 55(3), 615–623 (1989), Hiroshi Nakajima et al.). The 50% lethal dose ($LD_{50}$) of Ap4A measured by the Lichfield-Wilcoxon Method is 102 mg/kg (rat intravenous injection), so that the toxicity of Ap4A is extremely low.

As demonstrated in later examples, Ap4A is capable of increasing coronary blood flow even in a state of excessive myocardial ischemia, and also exhibits myocardial protection against ischemia, thereby improving myocardial ischemia through a mechanism which is different from that of adenosine.

Ap4A is degraded in vivo to ATP and AMP, which are eventually degraded to adenosine. Therefore it can be assumed that adenosine rather than Ap4A causes the amelioration of myocardial ischemia.

However, comparative tests concerning the amelioration effects of Ap4A and adenosine using mongrel dogs in a state of excessive ischemia have indicated that Ap4A exhibited a noticeable amelioration effect on myocardial ischemia in animals unaffected by adenosine. It was thus shown for the first time that Ap4A itself has an amelioration effect on myocardial ischemia, and is useful for curing ischemic myocardial disease end for decreasing the degree of myocardial ischemia.

Specific examples of such an ischemic myocardial disease include engine pectoris and acute, subacute, end chronic myocardial infarctions.

The agent of the present invention can be used not only at the onset of ischemia, but also in various cases where the ischemic syndrome occurs, such as after the use of a pump oxygenator, after PTCA (percutaneous transluminal coronary angioplasty) operation, and at the time of lowering of cardiac performance caused by a dysfunction of the pulmonary circulation, and also for maintaining coronary blood flow after the above-mentioned acute myocardial infarction and in the course of surgery which may possibly induce myocardial ischemia.

As mentioned previously, the agent according to the present invention comprises Ap4A or a salt thereof which is pharmaceutically acceptable in an effective amount.

Examples of such a salt include salts of alkali metals such as potassium salts and sodium salts; salts of alkaline earth metals such as magnesium salts; salts of copper hydroxide; salts of zinc hydroxide; salt of ammonia; salts of mono-, di- or tri-lower alkyl or hydroxyalkyl amines, such as mono-, di- and tri-methyl, ethyl or hydroxyethyl amine salts; salts of cycloalkyl amines such as pyrrolidinium salts; salts of other amines such as morphoinium salt; salts of alkyl imines; salts alkylene diamines; and various hydrates of these salts.

Of these salts, sodium salts such as Ap4A.nNa (n=1–4) and magnesium salts are preferable.

The term "effective amount of Ap4A" means such an amount of Ap4A as can substantially decrease the degree of ischemia.

In the case of intravenous administration and intracoronary administration, the usual dose is from 0.01 μg/kg/min to 1 mg/kg/min, although the range may vary. It is preferable that the intravenous administration be carried out by a dose of 1–100 μg/kg/min, and that the intracoronary administration be carried out by a dose of 0.1–30 μg/kg/min. The administration amount can generally be changed in accordance with the age, symptoms and weight of the patient, and other factors recognized as being relevant to ischemic myocardial disease.

The agent according to, the present invention may further comprise a pharmaceutically-acceptable carrier or diluent.

An example of such carrier is cyclodextrin, and examples of such diluent are physiologic saline solution, distilled water for injection, sterile purified water, and other liquids for transfusion.

When necessary, the agent according to the present invention may further comprise conventional additives such as stabilizing agents, tonicity agents, solubilizing agents, preservatives and buffer agents.

The dosage of the agent according to the present invention may be in the form of either a solid or a liquid. Examples of such dosage form are tablets, pills, granules, powders, capsules, suspensions, emulsions, injections, intravenous drip infusions, inhalations, sprays and suppositories.

The route of administration of the agent according to the present invention may be oral administration and parenteral administration. Examples of parenteral administration include intravenous injection, intra-arterial injection, and intra-nasal injection.

Other features of this invention will become apparent in the course of the following description of exemplary embodiments, which are given for illustration of the invention and are not intended to be limiting thereof.

Instrumentation

Mongrel dogs weighing 18–22 kg were anesthetized with pentobarbital sodium (30 mg/kg). The trachea was intubated, and the dog was ventilated with room air with oxygen. The chest was opened through the left fifth intercostal space, and the heart was suspended in a pericardial cradle. The left anterior descending coronary artery was cannulated and perfused with blood via the carotid artery through an extracorporeal bypass tube after heparinization (500 units/kg). Coronary blood flow (CBF) was measured with an electromagnetic flow probe attached to the bypass tube, and coronary perfusion pressure (CPP) was monitored at the tip of the coronary arterial cannula. A small, short collecting tube was cannulated into a small coronary vein near the center of the perfused area to sample coronary venous blood. The drained venous blood was collected in a reservoir placed at the level of the left atrium. A high fidelity of left ventricular pressure and its first derivative were measured by a micromanometer (model P-5, Konigsberg Instruments, Inc., Pasadena, Calif.) placed in the left ventricular cavity through the apex. A pair of ultrasonic crystals was placed in the center of the perfused area about 1 cm apart to measure myocardial segment length with an ultrasonic dimension gauge (5 MHz, Schuessler, Cardiff by the Sea, Calif.). End-diastolic length (EDL) was determined at the R wave of the electrocardiogram, and end-systolic length (ESL) was determined at the minimal dP/dt. Fractional shortening was calculated by (EDL-ESL)/EDL as an index of myocardial contractility of the perfused area.

Lactate was assessed by enzymatic assay (Hori et al., Am J Physiol 1986;250: H509–H518) in accordance with the following formula:

$$\frac{\left(\begin{array}{c}\text{Amount of lactate} \\ \text{in arterial blood}\end{array}\right) - \left(\begin{array}{c}\text{Amount of lactate} \\ \text{in venous blood}\end{array}\right)}{(\text{Amount of lactate in arterial blood})} \times 100\%$$

Namely, the lactate extraction ratio was obtained by coronary arteriovenous difference in lactate concentration multiplied by 100 and divided by arterial lactate concentration.

EXAMPLE 1

Coronary blood flow increase effect induced by Ap4A

After stabilization, a physiological saline solution prepared by dissolving Ap4A.4Na in physiological saline was continuously infused into the coronary artery, with the dosage thereof increased to 0.5, 1, 2, 4 and 8 µg/kg/min, and the changes in coronary blood flow were measured in order to assess the coronary blood flow increase effect of Ap4A.

In this nonischemic condition, as shown in TABLE 1, Ap4A is capable of significantly increasing the coronary blood flow dose-dependently in the dosage range of 0.5 to 8 µg/kg/min. This effect was also observed in the intravenous administration of Ap4A.

8-sulfophenyltheophylline (hereinafter referred to as 8-SPT) serving as adenosine $P_1$ receptor antagonist with a dose of 25 µg/kg/min was tested. The result was that the coronary blood flow increase effect of Ap4A was partially inhibited when 8-SPT was used in an amount by which the effect of adenosine was completely inhibited.

The above test was also repeated by replacing 8-SPT with $N^G$-nitro-L-arginine methyl ester (hereinafter referred to as L-NAME) serving as an endothelial-cell-induced nitric oxide (NO) synthesis inhibitor with a dose of 3 µg/kg/min(ic). The result was that the coronary blood flow increase effect of Ap4A was only slightly inhibited by L-NAME.

The above test was then repeated using 8-SPT and L-NAME in combination. The result was that the coronary blood flow increase effect of Ap4A was not completely inhibited even by the combined use of 8-SPT and L-NAME.

The specific results of the above tests are shown in TABLE 1.

TABLE 1

Coronary blood flow increase effect of Ap4A and effects of 8-SPT and L-NAME thereon

| Coronary blood flow (ml/100 g /min) | Control | 8-SPT and/or L-NAME | Ap4A (µg/kg/min) | | | | |
|---|---|---|---|---|---|---|---|
| | | | 0.5 | 1 | 2 | 4 | 8 |
| Untreated | 93.7 | | 104.1 | 122.2 | 137.6 | 158.9 | 202.2 |
| 8-SPT | 97.0 | 93.7 | 98.6 | 96.8 | 106.1 | 117.0 | 124.5 |
| L-NAME | 90.3 | 90.3 | 100.0 | 119.4 | 122.6 | 151.6 | 219.4 |
| 8-SPT + L-NAME | 97.1 | 97.1 | 97.1 | 108.6 | 102.9 | 114.3 | 120.0 |

N = 1 – 2

In view of the above results, it can be considered that the coronary blood flow increase effect of Ap4A is partly due to metabolites thereof such as adenosine. Results also clearly indicate that the coronary blood flow increase effect of Ap4A is partly attained by the unchanged Ap4A itself. In other words, the above results indicate that the coronary blood flow increase effect induced by Ap4A has a different mechanism from that induced by adenosine.

Changes in myocardial oxygen consumption ($M\dot{V}O_2$) (ml/100 g/min) caused by the administration of Ap4A were measured as shown in TABLE 2. The results shown in TABLE 2 indicate that the administration of Ap4A neither largely increased nor decreased myocardial oxygen consumption ($M\dot{V}O_2$), so that Ap4A is capable of maintaining the function of myocardial metabolism.

TABLE 2

Effects of Ap4A on myocardial oxygen consumption

| | Control | Ap4A (µg/kg/min) | | | | |
|---|---|---|---|---|---|---|
| | | 0.5 | 1 | 2 | 4 | 8 |
| Myocardial oxygen consumption (ml/100 g/min) | 9.1 | 9.9 | 9.0 | 8.7 | 8.7 | 9.5 |

EXAMPLE 2

Amelioration of myocardial ischemia by Ap4A

After stabilization, CPP was decreased with partial occlusion of the bypass tube to the left anterior descending coronary artery such that CBF decreased to one third of the control flow. The low CPP was maintained during this test.

10 minutes after the onset of myocardial ischemia, Ap4A was continuously infused into the coronary artery with a dose of 4 µg/kg/min for 10 minutes by use of the same physiological saline solution as employed in Example 1. Blood sampling from coronary veins and coronary arteries was conducted. Then the intracoronary administration of Ap4A was stopped. The lowered coronary perfusion pressure was further maintained for 10 minutes.

Ap4A exhibited a sufficient coronary blood flow improvement with a significant increment thereof from 30.4 ml/100 g/min to 48.2 ml/100 g/min as shown in TABLE 3.

Furthermore, Ap4A was capable of significantly preventing a decrease in myocardial fractional shortening and of recovering the same from 4.9 to 11.5% as shown in TABLE 3, so that Ap4A exhibited a cardiac muscle protection effect. The ischemia was factitious, so that when the administration of Ap4A was stopped, the model was returned to ischemia.

TABLE 3

Effects of Ap4A on coronary blood flow during ischemia

| | Control | Factitious ⅓ blood flow (ischemia) | | |
|---|---|---|---|---|
| | | ⅓ control | Ap4A 4 µg/kg/min | Administration stopped |
| Coronary blood flow (ml/100 g/min) | 90.5 | 30.4 | 48.2 | 31.9 |
| Myocardial fractional shortening (%) | 24.7 | 4.9 | 11.5 | 4.8 |
| Coronary perfusion pressure (mmHg) | 104 | 54 | 54 | 54 |

N = 2

The above test was repeated by replacing Ap4A with adenosine with the dosage thereof being changed to 4, 8 and 16 µg/kg/min.

The result was that even if the administration amount of adenosine was increased, there were no substantial changes in coronary blood flow and myocardial fractional shortening under such ischemic condition, suggesting that adenosine does not exhibit any therapeutic effects in excessive ischemic states, as shown in TABLE 4.

TABLE 4

Effects of adenosine on coronary blood flow during ischemia

|  | Control | Factitious ⅓ blood flow (ischemia) | | | |
|---|---|---|---|---|---|
|  |  | ⅓ control | Adenosine (µg/kg/min) | | |
|  |  |  | 4 | 8 | 16 |
| Coronary blood flow (ml/100 g/min) | 91.3 | 21.2 | 18.2 | 18.2 | 18.2 |
| Myocardial fractional shortening (%) | 26.9 | 5.3 | 5.9 | 3.9 | 5.3 |
| Coronary perfusion pressure (mmHg) | 93.0 | 57.0 | 56.0 | 56.0 | 56.0 |

As mentioned previously, in the above-mentioned experimental systems, lactate extraction ratio and pH of venous blood were measured at the time of the intracoronary administration of Ap4A and also at the time of the intracoronary administration of adenosine.

The results are shown in TABLE 5 and TABLE 6.

TABLE 5

Effects of ischemia on lactate extraction ratio and pH of venous blood and improvement thereof by Ap4A

|  | Control | Factitious ⅓ blood flow (ischemia) | | |
|---|---|---|---|---|
|  |  | ⅓ control | Ap4A | |
|  |  |  | 4 µg/kg/min | Administration stopped |
| Lactate extraction ratio (%) | 28.3 | −39.8 | −15.8 | −48.6 |
| pH of venous blood | 7.39 | 7.23 | 7.29 | 7.19 |

N = 2

TABLE 6

Effects of ischemia on lactate extraction ratio and effects of adenosine thereon

|  | Control | Factitious ⅓ blood flow (ischemia) | | | |
|---|---|---|---|---|---|
|  |  | ⅓ control | Adenosine (µg/kg/min) | | |
|  |  |  | 4 | 8 | 16 |
| Lactate extraction ratio (%) | 26.5 | −67.9 | −73.2 | −69.8 | −73.2 |
| pH of venous blood | 7.46 | 7.23 | 7.19 | 7.25 | 7.22 |

The results shown in TABLE 5 and TABLE 6 indicate that Ap4A exhibited an effect of preventing the worsening of the lactate extraction ratio (hereinafter referred to as LER) and the lowering of pH, which are caused by ischemia, with the improvement of LER from −39.8 to −15.8 and the improvement of pH from 7.23 to 7.29.

However, adenosine exhibited no such amelioration effects.

Japanese Patent Application No. 6-149971 filed Jun. 30, 1994, is hereby incorporated by reference.

What is claimed is:

1. A method for curing ischemic myocardial disease comprising administering to a patient suffering from ischemic myocardial disease an effective amount of diadenosine 5',5'''-p$^1$,p$^4$-tetraphosphate (Ap4A) of formula (I):

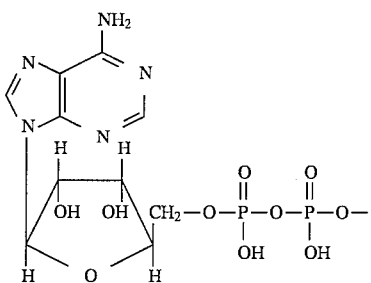

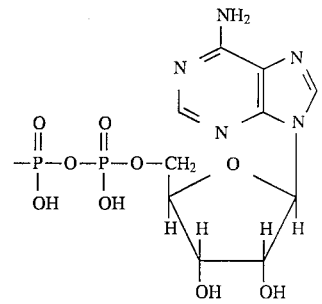

or a pharmaceutically-acceptable salt thereof.

2. The method as claimed in claim 1, wherein said salt is an alkali metal salt.

3. The method as claimed in claim 2, wherein said alkali metal salt is a sodium salt.

4. The method as claimed in claim 1, further comprising a pharmaceutically-acceptable carrier or diluent.

* * * * *

UNITED STATES PATENT AND TRADEMARK OFFICE
CERTIFICATE OF CORRECTION

PATENT NO. : 5,571,524
DATED : November 5, 1996
INVENTOR(S) : Masafumi KITAKAZE ET AL It is certified that error appears in the above-identified patent and that said Letters Patent is hereby corrected as shown below:

Column 1, line 20, "the tame of" should read --the time of--.

Column 1, line 24, "greaterthe the" should read --greater the--.

Column 1, line 44, "several tames prior" should read --several times prior--.

Column 3, line 18, "disease end for" should read --disease and for--.

Column 3, line 21, "subacute, end chronic" should read --subacute, and chronic--.

Signed and Sealed this

Ninth Day of June, 1998

Attest:

BRUCE LEHMAN

Attesting Officer

Commissioner of Patents and Trademarks